(12) United States Patent
Knevels et al.

(10) Patent No.: US 6,883,392 B2
(45) Date of Patent: Apr. 26, 2005

(54) SAMPLER FOR MELTS, IN PARTICULAR FOR SLAGS LYING ON A MOLTEN METAL

(75) Inventors: Johan Knevels, Bree (BE); Guido GustaafAntoon Cappa, Houthalen (BE); Frank Mingneau, Zonhoven (BE)

(73) Assignee: Heraeus Electro-Nite International N.V., Houthalen (BE)

( * ) Notice: Subject to any disclaimer, the term of this patent is extended or adjusted under 35 U.S.C. 154(b) by 72 days.

(21) Appl. No.: 10/340,416

(22) Filed: Jan. 10, 2003

(65) Prior Publication Data

US 2003/0131673 A1 Jul. 17, 2003

(30) Foreign Application Priority Data

Jan. 11, 2002 (DE) ......................................... 102 01 023

(51) Int. Cl.⁷ ................................................. G01N 1/12
(52) U.S. Cl. ................................ 73/864.53; 73/864.55; 73/864.59
(58) Field of Search ........................ 73/864.53–864.59, 73/DIG. 9

(56) References Cited

U.S. PATENT DOCUMENTS

| | | |
|---|---|---|
| 3,656,346 A | 4/1972 | Collins |
| 3,656,350 A | 4/1972 | Collins |
| 3,820,380 A | 6/1974 | Miller et al. |
| 4,179,931 A | 12/1979 | Moriya |
| 4,291,585 A * | 9/1981 | Kolb et al. ............... 73/863.23 |
| 4,361,053 A * | 11/1982 | Jones et al. ............... 73/864.53 |
| 5,979,253 A | 11/1999 | Knevels et al. |
| 6,370,973 B1 * | 4/2002 | Wunsch et al. .......... 73/864.53 |
| 6,811,742 B1 * | 11/2004 | Knevels ............... 73/DIG. 9 X |
| 2001/0020397 A1 * | 9/2001 | Cappa et al. ............. 73/864.58 |
| 2003/0062661 A1 * | 4/2003 | Knevels ........................ 266/79 |

FOREIGN PATENT DOCUMENTS

| | | | |
|---|---|---|---|
| DE | 28 40 745 B2 | 9/1980 | |
| DE | 34 02 818 A1 | 8/1985 | |
| DE | 197 52 743 A1 | 6/1999 | |
| DE | 100 49 253 A1 | 9/2001 | |
| FR | 2 026 247 | 9/1970 | |
| GB | 1235800 A * | 6/1971 | ........... B22D/19/00 |
| GB | 2 335 738 A | 9/1999 | |
| JP | 61077761 A | 4/1986 | |
| JP | 05273197 A | 10/1993 | |
| JP | 11304669 A | 11/1999 | |
| WO | WO 00/73765 A1 | 12/2000 | |

* cited by examiner

Primary Examiner—Thomas P. Noland
(74) Attorney, Agent, or Firm—Akin Gump Strauss Hauer & Feld, LLP

(57) ABSTRACT

A sampler is provided for melts, in particular for slags lying on a molten metal, the sampler having a single- or multi-part body for arrangement in a support. The sampler has an inlet and a sample chamber with two opposing chamber walls, wherein an inlet opening is arranged in one chamber wall. In order to make possible homogeneous and stable samples, an intermediate plate with at least one through opening is arranged inside of the sample chamber spaced from the chamber walls.

15 Claims, 2 Drawing Sheets

SAMPLER FOR MELTS, IN PARTICULAR FOR SLAGS LYING ON A MOLTEN METAL

BACKGROUND OF THE INVENTION

The invention relates to a sampler for melts, in particular for slags lying on a molten metal, the sampler having a single or multi-part body arranged in a support, an inlet and a sample chamber with two opposing chamber walls, wherein an inlet opening is arranged in one chamber wall.

Samplers of this type are known from German published patent application DE 100 49 253 A1. They are suitable in particular for the sampling of slags. Slags of this type contain, as a rule, gas bubbles. As a result, the samples taken, in many cases, become porous and brittle.

BRIEF SUMMARY OF THE INVENTION

Objectives of the invention include improving the known samplers and making possible more stable samples. These objectives are achieved according to the invention in that inside of the sample chamber, an intermediate plate is arranged spaced from the chamber walls and that the intermediate plate has at least one through opening. The through opening(s) cause(s) gas bubbles to be broken up and made smaller. The sample becomes more homogeneous, and the porosity decreases. In addition, the intermediate plate serves as an anchor for the sample, in particular a slag sample.

Expediently, the sample chamber is constructed as a cylinder, with its base surfaces having an approximately circular cross section, whose diameter is greater than the thickness (depth) of the sample chamber, and wherein the inlet opening is arranged approximately in the center of a chamber wall that forms a base surface. It is particularly advantageous if the intermediate plate is arranged transverse to the direction of the flow passing through the inlet opening into the sample chamber. In particular, it is expedient if at least one chamber wall is made of metal, in particular steel. A sample chamber with a ring-shaped sidewall made of metal is also expedient. The intermediate plate can have a plurality of through openings evenly distributed over the surface of the intermediate plate, so as to optimally break up the gas bubbles. The intermediate plate can be made of metal or ceramic, and the through openings can be approximately as large as the inlet opening.

In an advantageous embodiment the inlet is constructed conically or funnel-shaped, wherein the end with the smaller cross section faces the sample chamber. The sample chamber expediently has metal walls on all sides. The metal walls are preferably made of steel.

The sampler according to the invention effects an optimum breakup of the gas bubbles, and these are broken up at the intermediate plate. Also, the intermediate plate homogenizes the sample, and it stabilizes the sample after it is withdrawn, since slag is itself relatively brittle. The intermediate plate represents an additional cooling capacity, which is particularly necessary for high temperature slags or very fluid slags, as occur for example in vacuum furnaces, so that the slag rapidly cools and does not run out of the sample chamber after the sample is taken. Metallic sample chamber walls also facilitate rapid cooling and provide smooth sample chamber walls in order to obtain optimum surfaces for analysis. The outer body is made of foundry sand.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there is shown in the drawings an embodiment which is presently preferred. It should be understood, however, that the invention is not limited to the precise arrangements and instrumentalities shown. In the drawings.

DETAILED DESCRIPTION OF THE INVENTION

Figure 1:
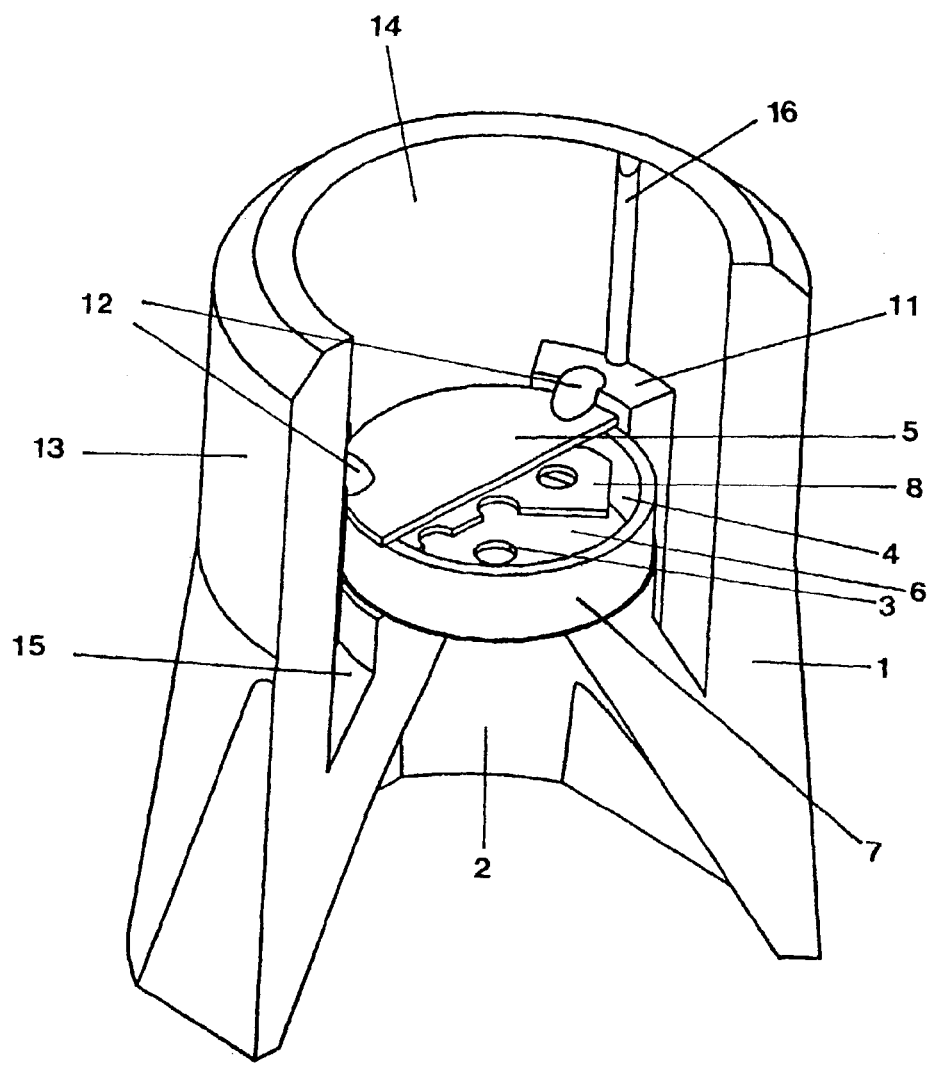
FIG. 1 is a sampler according to the invention, partially broken away to show the interior thereof.
Figure 2:
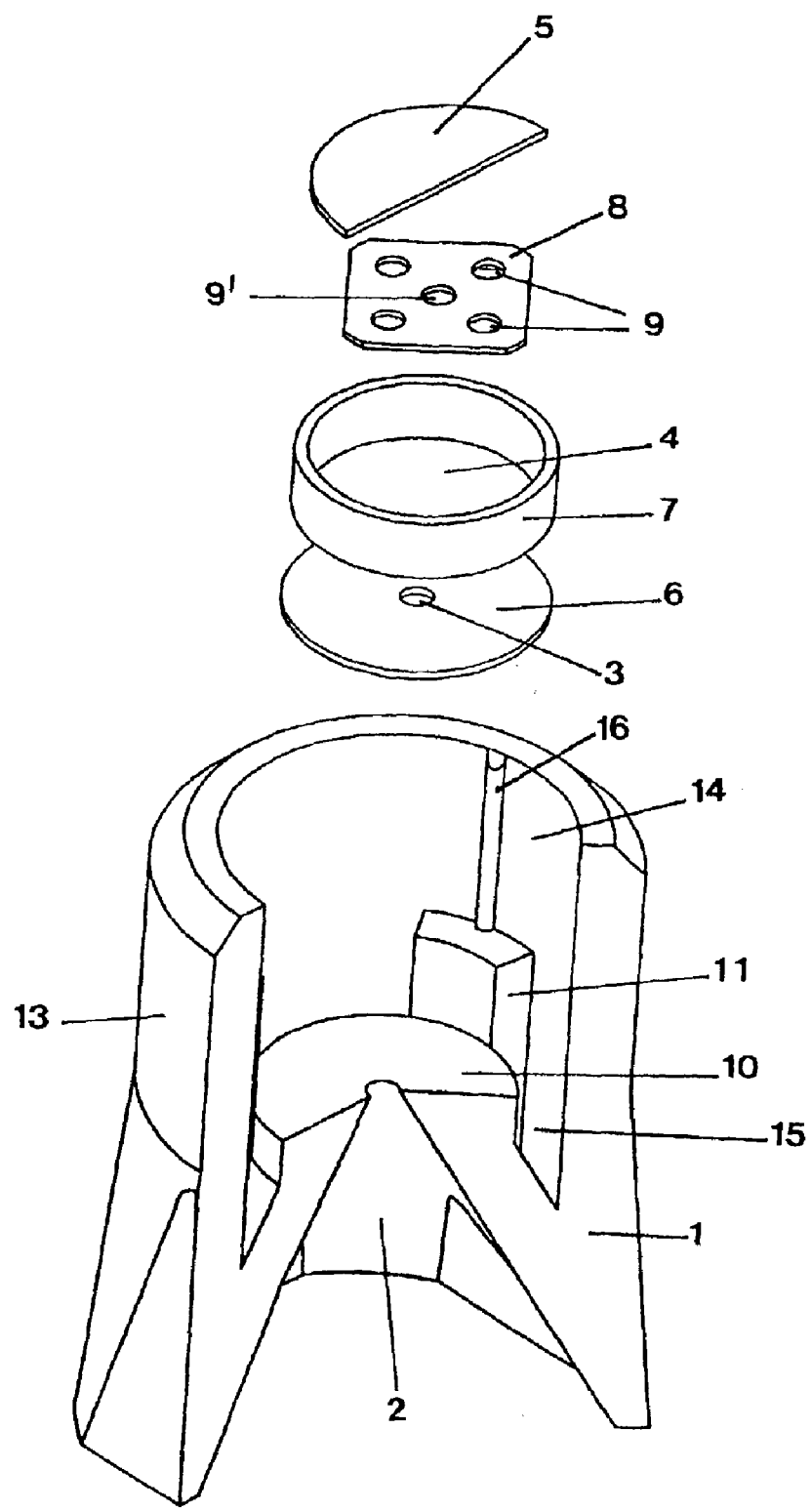
FIG. 2 is an exploded representation of the sampler of FIG. 1.

The body 1 of the sampler is manufactured from foundry sand. The sampler body 1 has a cone- or funnel-shaped inlet 2, which opens into a sample chamber 4 through an inlet opening 3. The sample chamber 4 is constructed disc-shaped (cylindrical) with a circular cross section. The chamber walls 5; 6 forming the base surfaces are made of steel, as is the ring-shaped sidewall 7.

Parallel to the base surfaces 5; 6, in the interior of the sample chamber 4, an intermediate plate 8 is arranged approximately centrally between the two base surfaces 5; 6. The intermediate plate 8 is made of steel and has a plurality of through openings 9, 9'. Around a central through opening 9' having a diameter of approximately 8 mm are arranged four other through openings 9 having a diameter of approximately 5 mm, preferably distributed evenly on a circular line. It is also possible to construct the intermediate plate 8 without a central through opening or to provide through openings in other arrangements. The intermediate plate 8 is anchored in the sample chamber 4 to the sidewall 7.

The base surface 6 of the sample chamber 4 sits on a seating surface 10 of the housing 1. Laterally, the sample chamber is held centered by guide elements 11. The base surface 5 is locked in place at fastening locations 12 on these guide elements 11, for example by cementing or pressing.

The sampler body 1 is held in the usual manner in a support, not shown in the drawing. The support is, for example, a cardboard tube. This tubular support can either surround the cylindrical exterior 13 of the sampler body 1 or it can be inserted into the body 1 and lie against its cylindrical inner wall 14. In the latter case, the support tube can be inserted up to slot 15, located between the external wall of the body 1 and the conical inlet 2. In order to fix the support tube laterally, the inner side of the body 1 has a bead 16 parallel to the axis, by which the support tube can be firmly fixed.

In use, the sampler is introduced into the slag layer from above, and the slag rises within the cone- or funnel-shaped inlet 2 upwardly into the sample chamber 4. The conical or funnel shape ensures, in a known manner, that the slag is gathered over a large area and that no molten metal makes its way into the sample chamber.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A sampler for melts, comprising a single- or multi-part sampler body (1) having an inlet (2) and a sample chamber (4), the sample chamber having two opposing chamber walls (5,6), an inlet opening (3) arranged in one of the chamber walls, and an intermediate plate (8) arranged inside the sample chamber (4) and spaced from the chamber walls (5; 6), wherein the intermediate plate (8) has at least one through opening (9; 9'), and wherein the at least one through opening (9; 9') is large enough to allow passage of the melt.

2. The sampler according to claim 1, wherein the sample chamber (4) has a shape of a cylinder having an approximately circular cross section, wherein the opposing chamber walls (5,6) form base surfaces of the cylinder having a diameter larger than a depth of the sample chamber (4), and wherein the inlet opening (3) is arranged approximately centrally of one of the chamber wall (5; 6) forming one of the base surfaces.

3. The sampler according to claim 2, wherein the sample chamber (4) has a least on ring-shaped sidewall (7) made of metal.

4. The sampler according to claim 1, wherein at least one chamber wall (5; 6) is made of metal.

5. The sampler according to claim 4, wherein the metal is steel.

6. The sampler according to claim 1, wherein the intermediate plate (8) is arranged transverse to a direction of flow through the inlet opening (3) into the sample chamber (4).

7. The sample according to claim 1, wherein the intermediate plate (8) has a plurality of through openings (9; 9') substantially evenly distributed over a major surface of the intermediate plate (8).

8. The sampler according to claim 1, wherein the intermediate plate (8) is made of a material selected from the group consisting of metal and ceramic.

9. The sampler according to claim 1, wherein the at least one through opening (9; 9') has a diameter approximately as large as a diameter of the inlet opening (3).

10. The sampler according to claim 1, wherein the inlet (2) has a conical shape with an end having a smaller cross section facing the sample chamber (4).

11. The sampler according to claim 1, wherein the sample chamber (4) has metal walls all around.

12. The sampler according to claim 1, which is adapted for sampling slag lying on a molten metal.

13. The sampler according to claim 1, which is adapted for arrangement in or on a tubular support.

14. The sampler according to claim 1, wherein the at least one through opening (9; 9') is a central opening having a diameter of approximately 8 mm.

15. The sampler according to claim 14, wherein the central opening is surrounded by four additional openings having a diameter of approximately 5 mm.

* * * * *